United States Patent
Denman

(10) Patent No.: US 10,722,040 B2
(45) Date of Patent: Jul. 28, 2020

(54) WEARABLE ELBOW AND SHOULDER NON-IMPINGEMENT PILLOW

(71) Applicant: Timothy Aaron Denman, Huntsville, AL (US)

(72) Inventor: Timothy Aaron Denman, Huntsville, AL (US)

(*) Notice: Subject to any disclaimer, the term of this patent is extended or adjusted under 35 U.S.C. 154(b) by 35 days.

(21) Appl. No.: 16/000,216

(22) Filed: Jun. 5, 2018

(65) Prior Publication Data

US 2018/0344037 A1 Dec. 6, 2018

Related U.S. Application Data

(60) Provisional application No. 62/514,990, filed on Jun. 5, 2017.

(51) Int. Cl.
| | | |
|---|---|---|
| *F16M 13/00* | (2006.01) | |
| *A47C 16/00* | (2006.01) | |
| *A61F 7/02* | (2006.01) | |
| *A61F 7/00* | (2006.01) | |

(52) U.S. Cl.
CPC .............. *A47C 16/00* (2013.01); *A61F 7/02* (2013.01); *A61F 2007/0029* (2013.01); *A61F 2007/0032* (2013.01); *A61F 2007/0282* (2013.01)

(58) Field of Classification Search
CPC .... A61G 13/12; A61G 7/075; A61G 13/1255; A61G 5/125
USPC ............ 248/118, 118.1, 118.3, 118.5; 5/646, 5/647; 602/20
See application file for complete search history.

(56) References Cited

U.S. PATENT DOCUMENTS

| | | | |
|---|---|---|---|
| 3,903,878 A * | 9/1975 | Spann | A61F 13/069 602/21 |
| 4,375,809 A * | 3/1983 | Meals | A61F 5/3753 128/845 |
| 4,617,691 A | 10/1986 | Monti et al. | |
| D287,641 S * | 1/1987 | Schaefer | 5/647 |
| 4,783,866 A | 11/1988 | Simmons et al. | |
| 5,085,214 A | 2/1992 | Barrett | |
| 5,437,070 A | 8/1995 | Rempp | |
| 5,882,324 A | 3/1999 | Baranowski | |
| 6,041,458 A | 3/2000 | Vickers et al. | |
| 7,356,849 B2 * | 4/2008 | Morrow | A61F 5/0118 2/16 |
| 7,426,764 B2 | 9/2008 | Ekins | |
| 7,428,763 B2 | 9/2008 | Hightower | |
| 7,563,236 B2 | 7/2009 | Kazmierczak et al. | |
| 7,581,267 B2 | 9/2009 | Rubio | |
| 7,962,984 B2 | 6/2011 | Popp | |
| D643,588 S | 8/2011 | Malcolm et al. | |

(Continued)

*Primary Examiner* — Steven M Marsh
(74) *Attorney, Agent, or Firm* — Merchant & Gould P.C.

(57) ABSTRACT

A pillow for supporting a user's arm. The pillow includes a body defining a substantially circumferential shape around an aperture. The body includes a substantially flat support base, a first curved arm, and a second curved arm. The substantially flat support base defines a substantially flat geometry extending along a first axis to stably contact a substantially flat surface while a user's arm is inserted through the aperture, the body comprising an open state and a closed state. The first curved arm defines a first contact face with a first fastener. The second curved arm defines a second contact face with a second fastener. The first fastener is releasably fastened to the second fastener.

23 Claims, 3 Drawing Sheets

(56) References Cited

U.S. PATENT DOCUMENTS

| | | |
|---|---|---|
| 9,326,906 B2 | 5/2016 | Thanas |
| 2006/0226305 A1* | 10/2006 | Sheybani .............. A61F 5/0118 248/118.5 |
| 2008/0217492 A1* | 9/2008 | Stearns .............. A47B 21/0371 248/118.5 |
| 2014/0251341 A1 | 9/2014 | Simonian |

* cited by examiner

WEARABLE ELBOW AND SHOULDER NON-IMPINGEMENT PILLOW

RELATED APPLICATIONS

Under provisions of 35 U.S.C. § 119(e), Applicants claim the benefit of U.S. provisional application No. 62/514,990, filed Jun. 5, 2017, which is incorporated herein by reference.

TECHNICAL FIELD

The present disclosure relates to a wearable elbow and shoulder pillow which promotes healing and provides comfort and relief while sleeping or resting.

BACKGROUND

Doctors often prescribe elbow and shoulder restraints that help a patient immediately after surgery. However, after a period of time, depending on the injury and complexity of the surgery, a patient goes from using a very bulky and uncomfortable restraint to sleeping with little or no support. Patients often aggravate or reinjure themselves during this time and healing is delayed. In addition, individuals often suffer minor shoulder and elbow injuries that do not require surgery (i.e., tennis elbow, bursitis, muscle pulls, etc.). Unfortunately, instead of sleep providing healing, the injury is further aggravated by sleeping in awkward positions. Accordingly, improvements are needed.

SUMMARY

A wearable elbow and shoulder pillow which promotes healing and provides comfort and relief while sleeping or resting. The pillow reduces the effects and duration of shoulder impingement and also increases blood flow to the affected areas in the elbow, arm, and shoulder. An insertable hot/cold pack used in concert with the pillow can also help reduce ulnar nerve pain or pain at any area on the arm between the elbow and shoulder.

The wearable elbow and shoulder non impingement pillow is a horseshoe shaped pillow that is typically worn just above the elbow. It is the size of an average travel or neck pillow and it adjusts to the size of the wearer's arm. The pillow comfortably promotes the optimal arm position while sleeping or at rest. The pillow is lightweight and easily transportable. It takes up very little space when seated or lying down. The pillow is easily adjustable so it can be worn comfortably by people with large or small arms. A pocket is also provided for a hot/cold pack so heat or ice can be applied to the affected area. The pillow has a stable base so your arm naturally rests in the optimal position without using bulky and uncomfortable harnesses and straps. The pillow very simply fits on your arm and its benefits and intended functions are easy to explain and understand. It is small and provides similar benefits to much more complex devices and contraptions.

The pillow can be used to keep from irritating the shoulder before surgery, or even to help reduce the irritation of an inflamed elbow or shoulder. It can possibly keep someone from having surgery, impingement, or frozen shoulder due to continually irritating their elbow or shoulder.

The pillow is designed to enhance circulation, but it should be worn above the elbow (towards the shoulder) instead of on the forearm. The pillow also has much more padding, so the shoulder and elbow are stabilized while at rest. The main purpose of the pillow is to provide better circulation and more comfort. The pillow is designed to stabilize the shoulder and elbow to reduce irritation. Additionally, the pillow can be worn over other parts of the body as needed, for example shoulders and legs.

The pillow allows a user's arm to rest at the optimal position. This position helps keep a user from rolling over on her arm, which could further aggravate her elbow or shoulder. If worn on the upper part of the elbow, this pillow provides slight elevation that increases needed blood flow and reduces pain. Because the pillow adjusts for small or large arms, it stays on her arm when she moves in her sleep. It can also be worn on the right or left arm and works for people who sleep mostly on their side or back.

According to aspects of the invention, the present disclosure relates to a pillow for supporting a user's arm comprising an elbow on a substantially flat surface, the pillow comprising a body defining a substantially circumferential shape around an aperture, the body comprising a substantially flat support base, a first curved arm, and a second curved arm, the substantially flat support base defines a substantially flat geometry extending along a first axis to stably contact a substantially flat surface while a user's arm is inserted through the aperture, the body comprising an open state and a closed state; wherein, the first curved arm extends between a free end and a fixed end fixed to a first end of the support base, the first curved arm free end defining a first contact face comprising a first fastener, the first contact face defining a first length; wherein, the second curved arm extends between a free end and a fixed end fixed to a second end of the support base, the second curved arm free end defining a second contact face comprising a second fastener, the second contact face defining a second length, the first contact face first length being substantially equal to the second contact face second length, the first fastener being releasably fastened to the second fastener.

According to further aspects of the invention, the present disclosure relates to a pillow for supporting a user's arm comprising an elbow on a substantially flat surface, the pillow comprising a body defining a substantially circumferential shape around an aperture, the body comprising a support base, a first arm, and a second arm, the support base comprises a substantially flat contact surface extending along a first axis to stably contact a substantially flat surface while a user's arm is inserted through the aperture, the body comprising an open state and a closed state; wherein, the first arm extends between a free end and a fixed end fixed to a first end of the support base, the first arm free end defining a first contact face comprising a first fastener, the first contact face defining a first length; wherein, the second arm extends between a free end and a fixed end fixed to a second end of the support base, the second arm free end defining a second contact face comprising a second fastener, the second contact face defining a second length, the first contact face first length being substantially equal to the second contact face second length, the first fastener being releasably fastened to the second fastener; wherein the first fastener and the second fastener are adjustable to a plurality of engagement positions with respect to each other, wherein the adjustable engagement positions adjustably define the geometry of the aperture in the body.

According to still further aspects of the invention, the present disclosure relates to a pillow for supporting a user's arm comprising an elbow on a substantially flat surface, the pillow comprising a body defining a substantially circumferential shape around an aperture, the body comprising a substantially flat support base, a first curved arm, and a second curved arm, the substantially flat support base defines a substantially flat geometry extending along a first axis to stably contact a substantially flat surface while a user's arm is inserted through the aperture, the body comprising an open state and a closed state; wherein, the first curved arm extends between a free end and a fixed end fixed to a first end of the support base, the first curved arm free end defining a first contact face comprising a first fastener, the first contact face defining a first length; wherein, the second curved arm extends between a free end and a fixed end fixed to a second end of the support base, the second curved arm free end defining a second contact face comprising a second fastener, the second contact face defining a second length, the first contact face first length being substantially equal to the second contact face second length, the first fastener being releasably fastened to the second fastener; wherein the second fastener extends along a second length, and the first fastener extends along a first length, the second fastener second length being longer than the first fastener first length; wherein the first curved arm first contact face is oriented along a second axis that is oblique with respect to the support base first axis, and the second curved arm second contact face is oriented along a third axis that is oblique with respect to the support base first axis; wherein the first fastener and the second fastener are adjustable to a plurality of engagement positions with respect to each other, wherein the adjustable engagement positions adjustably define the geometry of the aperture in the body; wherein the aperture defines a height that is adjustable by adjustment of the contact position between the first fastener and the second fastener with respect to each other.

DESCRIPTION OF EXAMPLE EMBODIMENTS

Figure 1:
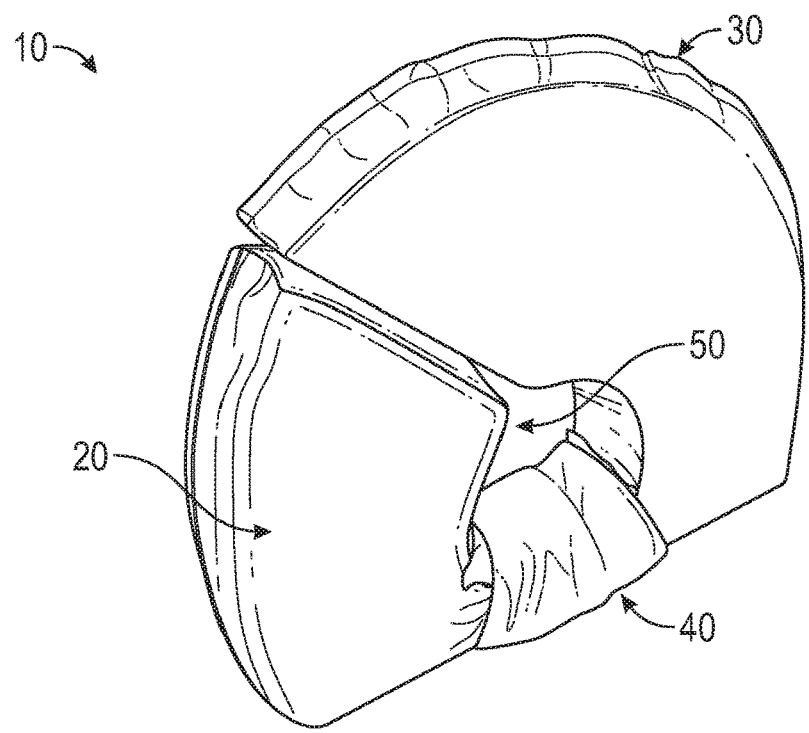
FIG. 1 is a schematic diagram of an adjustable pillow according to an example embodiment of the present invention, shown from a perspective view and in a closed state.
Figure 2:
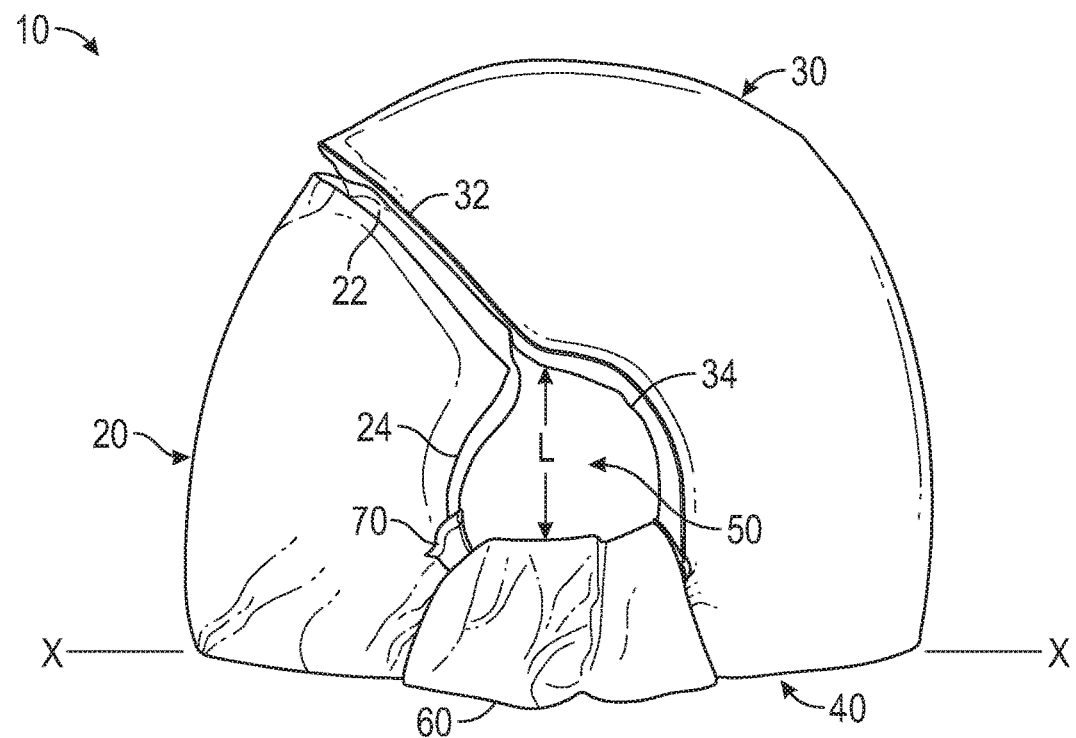
FIG. 2 is a side view of the adjustable pillow shown in FIG. 1.
Figure 3:
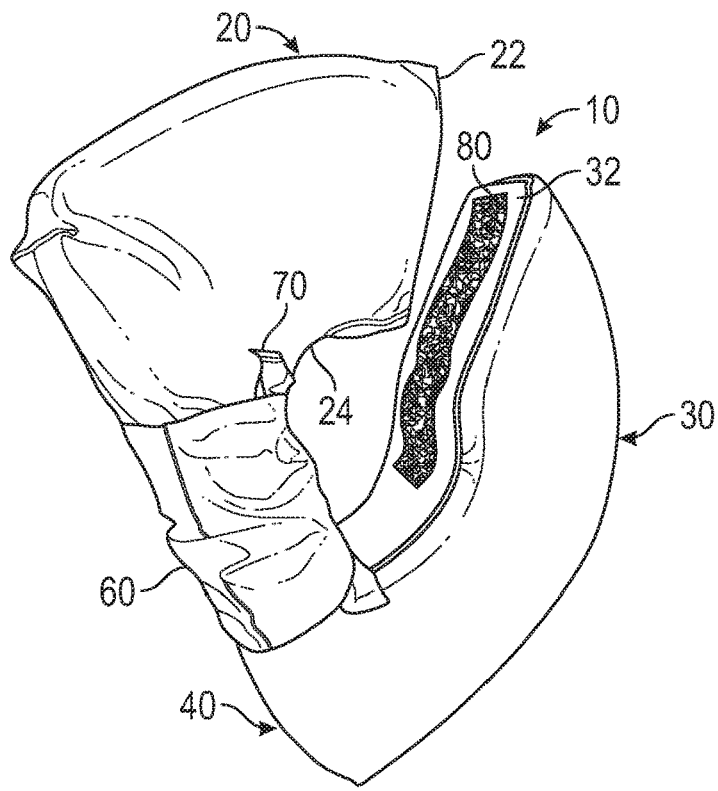
FIG. 3 is a perspective view of the adjustable pillow in FIG. 1, showing the pillow in an open state.
Figure 4:
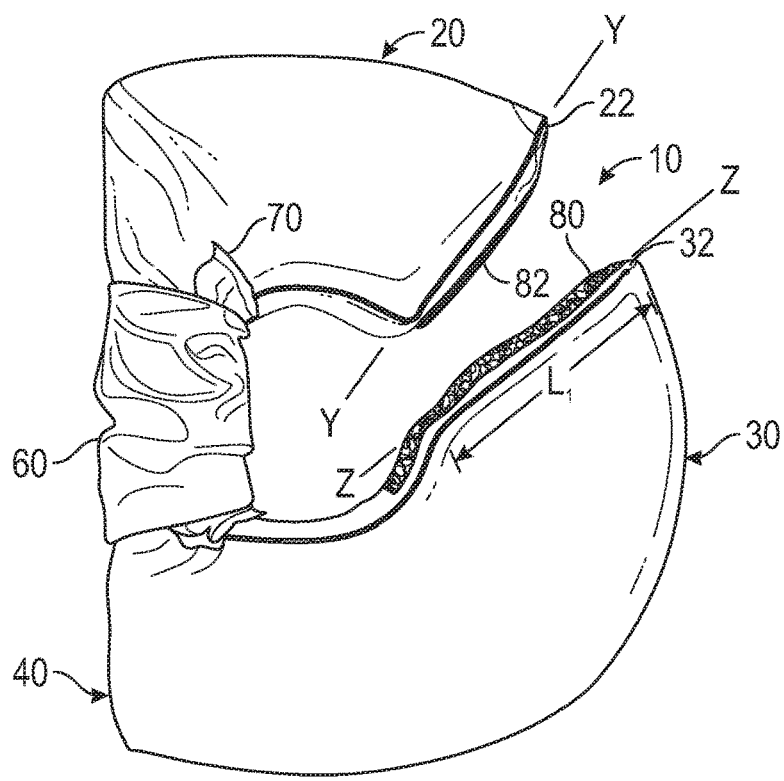
FIG. 4 is a side view of the adjustable pillow in an open state shown in FIG. 3.
Figure 5:
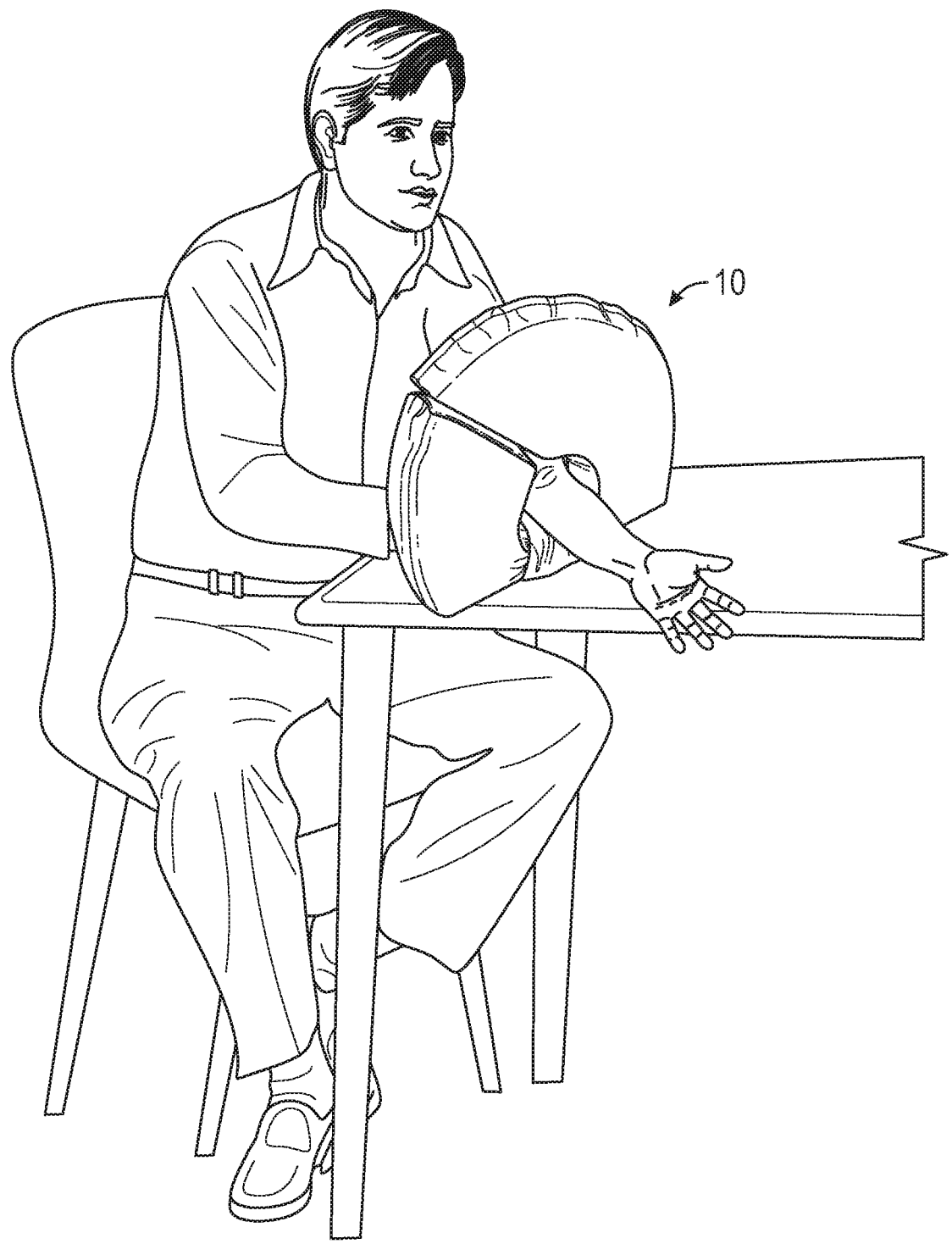
FIG. 5 is a schematic diagram of the adjustable pillow shown in FIG. 1, shown in use receiving a user's arm.

In reference to FIGS. 1-5, an example embodiment of the present disclosure relates to a pillow 10 for supporting a user's arm comprising an elbow on a substantially flat surface. The illustrated pillow 10 includes a body defining a substantially circumferential shape around an aperture 50. The body includes a substantially flat support base 40, a first curved arm 20, and a second curved arm 30. The substantially flat support base 40 defines a substantially flat geometry extending along a first axis X to stably contact a substantially flat surface while a user's arm is inserted through the aperture 50. The aperture 50 can alternate between an open state (FIGS. 3-4) and a closed state (FIGS. 1-2).

As illustrated, the first curved arm 20 extends between a free end and a fixed end that is fixed to a first end of the support base 40. The first curved arm 20 free end defines a first contact face 22 that includes a first fastener 82. The first contact face 22 defines a first length.

As illustrated, the second curved arm 30 extends between a free end and a fixed end that is fixed to a second end of the support base 40. The second curved arm 30 free end defines a second contact face 32 that includes a second fastener 80. The second contact face 32 defines a second length $L_1$. The first contact face 22 first length is substantially equal to the second contact face 32 second length $L_1$. The first fastener 82 is releasably fastened to the second fastener 80.

A preferred length of the first and second contact faces 22, 32 is between about 8 cm and 12 cm, and more preferably about 10 cm.

When the first and second contact faces 22, 32 are symmetrically aligned, the length of the first and second attachment faces are substantially equal to the length (or height) L from the upper surface of the support base 40 to the upper-most point in the aperture 50. When the first and second contact faces 22, 32 are adjusted lengthwise with respect to each other, this length L from the upper surface of the support base 40 to the upper-most point in the aperture 50 will also adjust, increasing or decreasing accordingly. In a natural state, the aperture length L is substantially equal to the first contact face 22 first length and the second contact face 32 second length $L_1$ when the first contact face and the second contact face are symmetrically engaged with respect to each other.

The geometry of the aperture 50 is defined by the upper surface of the support base 40, the inner surface 24 of the first curved arm 20, and the inner surface 34 of the second curved arm 30.

As illustrated, the second fastener 80 extends along a second length that can be longer than the second contact face 32 second length $L_1$, and extends partially into the inner surface 34 of the second contact face. The first fastener 82 extends along a first length, preferably substantially similar to the length of the first contact face 32 first length. As a result, the second fastener 80 is preferably longer than the first fastener 82.

As illustrated, the first curved arm 20 first contact face 22 is preferably oriented along a second axis Y that is oriented along an oblique angle with respect to the support base first axis X. The second curved arm 30 second contact face 32 is preferably oriented along a third axis Z that is also oriented along an oblique angle with respect to the support base first axis. Second axis Y and third axis Z are substantially parallel when the pillow 10 is in the closed state. (FIGS. 1-2).

The first fastener 82 and the second fastener 80 are adjustable to a plurality of engagement positions with respect to each other. For example, the first fastener 82 and the second fastener 80 can be adjusted to engage each other along each other's length to generate a variety of different geometries of the aperture 50.

As illustrated, the first curved arm 20 can have a different length, between the fixed end and the free end, than the second curved arm 30. As illustrated, the second curved arm 30 is longer than the first curved arm 20.

As illustrated, a thermal transfer element 70 can be removably positioned within the aperture 50, such that a user's arm contacts the thermal transfer element when inserted through the aperture. A retainer 60, for example a sleeve, can retain the thermal transfer element 70 in position within the aperture 50. The thermal transfer element 70 can deliver cooling or heating energy to the arm or elbow of a user.

The first fastener 82 and the second fastener 80 can be hook and loop structures which can be releasably connected. Alternatively, the first and second fasteners can be other fasteners which allow for releasable connection.

The pillow 10 can be formed by a single piece of cushioning material, for example foam, which forms the shape of the support base 40, the first arm 20 and the second arm 30. The piece of foam can be cut, preferably diagonally, to form the contact faces 22, 32 on the first and second arms 20, 30. The piece of foam could then be protected by a cover, which can be formed of a soft by durable material, such as cloth or nylon. The retainer 60 can be made of a similar material, and slip over the support base 40 from one of the first or second arms 20, 30.

ELEMENT NUMBERS

10 Pillow
20 First Arm
22 First Contact Face
24 First Section
30 Second Arm
32 Second Contact Face
34 Second Section
40 Support Base
50 Aperture
60 Retainer
70 Outer Wall
80 Second Fastener
82 First Fastener

I claim:

1. A pillow for supporting a user's arm comprising an elbow on a substantially flat surface, the pillow comprising:
   a body defining a substantially circumferential shape around an aperture, the body comprising a substantially flat support base, a first curved arm, and a second curved arm, the substantially flat support base defining a substantially flat geometry extending along a first axis to stably contact the substantially flat surface while a user's arm is inserted through the aperture, the body comprising an open state and a closed state;
   wherein, the first curved arm extends between a free end and a fixed end fixed to a first end of the support base, the first curved arm free end defining a first contact face comprising a first fastener, the first contact face defining a first length;
   wherein, the second curved arm extends between a free end and a fixed end fixed to a second end of the support base, the second curved arm free end defining a second contact face comprising a second fastener, the second contact face defining a second length, the first contact face first length being substantially equal to the second contact face second length, the first fastener being releasably fastened to the second fastener; and
   wherein the first fastener and the second fastener are adjustable to a plurality of engagement positions with respect to each other, wherein the adjustable engagement positions adjustably define the geometry of the aperture in the body.

2. The pillow of claim 1, wherein the second fastener extends along a second length, and the first fastener extends along a first length, the second fastener second length being longer than the first fastener first length.

3. The pillow of claim 2, wherein the first fastener first length is substantially equal to the first contact face first length, and the second fastener second length is longer than the second contact face second length.

4. The pillow of claim 1, wherein the first curved arm first contact face is oriented along a second axis that is oblique with respect to the support base first axis, and the second curved arm second contact face is oriented along a third axis that is oblique with respect to the support base first axis.

5. The pillow of claim 1, wherein the first curved arm is a different length than the second curved arm.

6. The pillow of claim 5, wherein the second curved arm is longer than the first curved arm.

7. The pillow of claim 1, wherein the aperture comprises a geometry that is defined by the support base, the first curved arm, and the second curved arm.

8. The pillow of claim 1, wherein the aperture defines a height that is adjustable by adjustment of the contact position between the first fastener and the second fastener with respect to each other.

9. The pillow of claim 8, wherein the aperture height is substantially the same as the first contact face first length and the second contact face second length when the first contact face and the second contact face are symmetrically engaged with respect to each other.

10. The pillow of claim 1, further comprising a thermal transfer element removably positioned within the aperture, wherein a user's arm contacts the thermal transfer element when inserted through the aperture.

11. The pillow of claim 10, further comprising a retainer, wherein the retainer retains the thermal transfer element in position within the aperture.

12. The pillow of claim 1, wherein the first fastener and the second fastener are hook and loop structures.

13. A pillow for supporting a user's arm comprising an elbow on a substantially flat surface, the pillow comprising:
    a body defining a substantially circumferential shape around an aperture, the body comprising a support base, a first arm, and a second arm, the support base comprising a substantially flat contact surface extending along a first axis to stably contact the substantially flat surface while the user's arm is inserted through the aperture, the body comprising an open state and a closed state;
    wherein, the first arm extends between a free end and a fixed end fixed to a first end of the support base, the first arm free end defining a first contact face comprising a first fastener, the first contact face defining a first length;
    wherein, the second arm extends between a free end and a fixed end fixed to a second end of the support base, the second arm free end defining a second contact face comprising a second fastener, the second contact face defining a second length, the first contact face first length being substantially equal to the second contact face second length, the first fastener being releasably fastened to the second fastener; and
    wherein the first fastener and the second fastener are adjustable to a plurality of engagement positions with respect to each other, wherein the adjustable engagement positions adjustably define the geometry of the aperture in the body.

14. The pillow of claim 13, wherein the first arm first contact face is oriented along a second axis that is oblique with respect to the support base first axis, and the second arm second contact face is oriented along a third axis that is oblique with respect to the support base first axis.

15. The pillow of claim 13, wherein the aperture defines a height that is adjustable by adjustment of the contact position between the first fastener and the second fastener with respect to each other, wherein the aperture height is substantially the same as the first contact face first length and the second contact face second length when the first contact face and the second contact face are symmetrically engaged with respect to each other.

16. The pillow of claim 13, further comprising a thermal transfer element removably positioned within the aperture, wherein the user's arm contacts the thermal transfer element when inserted through the aperture.

17. A pillow for supporting a user's arm comprising an elbow on a substantially flat surface, the pillow comprising:
- a body defining a substantially circumferential shape around an aperture, the body comprising a substantially flat support base, a first curved arm, and a second curved arm, the substantially flat support base defining a substantially flat geometry extending along a first axis to stably contact the substantially flat surface while the user's arm is inserted through the aperture, the body comprising an open state and a closed state;
- wherein, the first curved arm extends between a free end and a fixed end fixed to a first end of the support base, the first curved arm free end defining a first contact face comprising a first fastener, the first contact face defining a first length;
- wherein, the second curved arm extends between a free end and a fixed end fixed to a second end of the support base, the second curved arm free end defining a second contact face comprising a second fastener, the second contact face defining a second length, the first contact face first length being substantially equal to the second contact face second length, the first fastener being releasably fastened to the second fastener;
- wherein the second fastener extends along a second length, and the first fastener extends along a first length, the second fastener second length being longer than the first fastener first length;
- wherein the first curved arm first contact face is oriented along a second axis that is oblique with respect to the support base first axis, and the second curved arm second contact face is oriented along a third axis that is oblique with respect to the support base first axis;
- wherein the first fastener and the second fastener are adjustable to a plurality of engagement positions with respect to each other, wherein the adjustable engagement positions adjustably define the geometry of the aperture in the body; and
- wherein the aperture defines a height that is adjustable by adjustment of the contact position between the first fastener and the second fastener with respect to each other.

18. The pillow of claim 17, wherein the aperture height is substantially the same as the first contact face first length and the second contact face second length when the first contact face and the second contact face are symmetrically engaged with respect to each other.

19. The pillow of claim 17, further comprising a thermal transfer element removably positioned within the aperture, wherein the user's arm contacts the thermal transfer element when inserted through the aperture.

20. A pillow comprising:
- a body defining a substantially circumferential shape around an aperture, the body comprising a substantially flat support base, a first curved arm, and a second curved arm, the substantially flat support base defining a substantially flat geometry extending along a first axis, the body comprising an open state and a closed state;
- wherein, the first curved arm extends between a free end and a fixed end fixed to a first end of the support base, the first curved arm free end defining a first contact face comprising a first fastener;
- wherein, the second curved arm extends between a free end and a fixed end fixed to a second end of the support base, the second curved arm free end defining a second contact face comprising a second fastener; and
- wherein the first fastener and the second fastener are adjustable to a plurality of engagement positions with respect to each other, wherein the adjustable engagement positions adjustably define a size of the aperture in the body.

21. The pillow of claim 20, wherein the first and second arms have different lengths, and wherein the first and second contact faces meet at a reference plane that is oriented at an oblique angle relative to the first axis.

22. The pillow of claim 20, wherein the first and second arms have different lengths, and wherein the first and second contact faces meet at a reference plane that does not intersect a center of the aperture defined by the body.

23. The pillow of claim 20, wherein the support base has a length along the first axis that is longer than a thickness of the body measured in an orientation extending along a center axis of the aperture defined by the body.

\* \* \* \* \*